United States Patent [19]

Pipko

[11] Patent Number: 4,571,186
[45] Date of Patent: Feb. 18, 1986

[54] PRECISION ATTACHMENT FOR DENTURE CONSTRUCTION

[76] Inventor: Donald J. Pipko, #20H Chatham Towers, Pittsburgh, Pa. 15219

[21] Appl. No.: 698,326

[22] Filed: Feb. 5, 1985

[51] Int. Cl.$^4$ .............................................. A61C 13/22
[52] U.S. Cl. ..................................... 433/181; 433/213
[58] Field of Search ................ 433/182, 181, 172, 213

[56] References Cited

U.S. PATENT DOCUMENTS

| | | | |
|---|---|---|---|
| 1,693,845 | 12/1928 | Kellner et al. | 433/182 |
| 3,271,858 | 9/1966 | Simmons | 433/172 |
| 3,710,446 | 1/1973 | Poreromo | 433/182 |
| 4,474,499 | 10/1984 | Pedrazzini | 433/213 |

FOREIGN PATENT DOCUMENTS 3034434 4/1982 Fed. Rep. of Germany ...... 433/181

*Primary Examiner*—John J. Wilson
*Attorney, Agent, or Firm*—Reed, Smith, Shaw & McClay

[57] ABSTRACT

A prosthesis construction assembly for use in placement and alignment of dental bridge components for the fabrication of human tooth replacements, having a female member adapted to be deposited in a cavity provided in the distal side of an anchor tooth, with its longitudinal recess having two parallel side walls and a rounded mesial wall somewhat longer than the side walls so as to provide an end well in which a male member can pivot; and the male member having a rod portion also with a rounded first end and being sized to permit its sliding engagement and retention within the recess of said female portion; an outwardly oriented second flange portion integral with one arc of the rod portion surface and not extending beyond the point of said first rounded end. The second flange is adapted to provide a sliding abutment to the external surface of said first flange. An elongated bar portion is integrally attached to the other end of said male portion and abuts the proximal end of the second flange; and a transverse bar is disposed intermediate the ends of the mandrel portion and pinned thereto.

5 Claims, 10 Drawing Figures

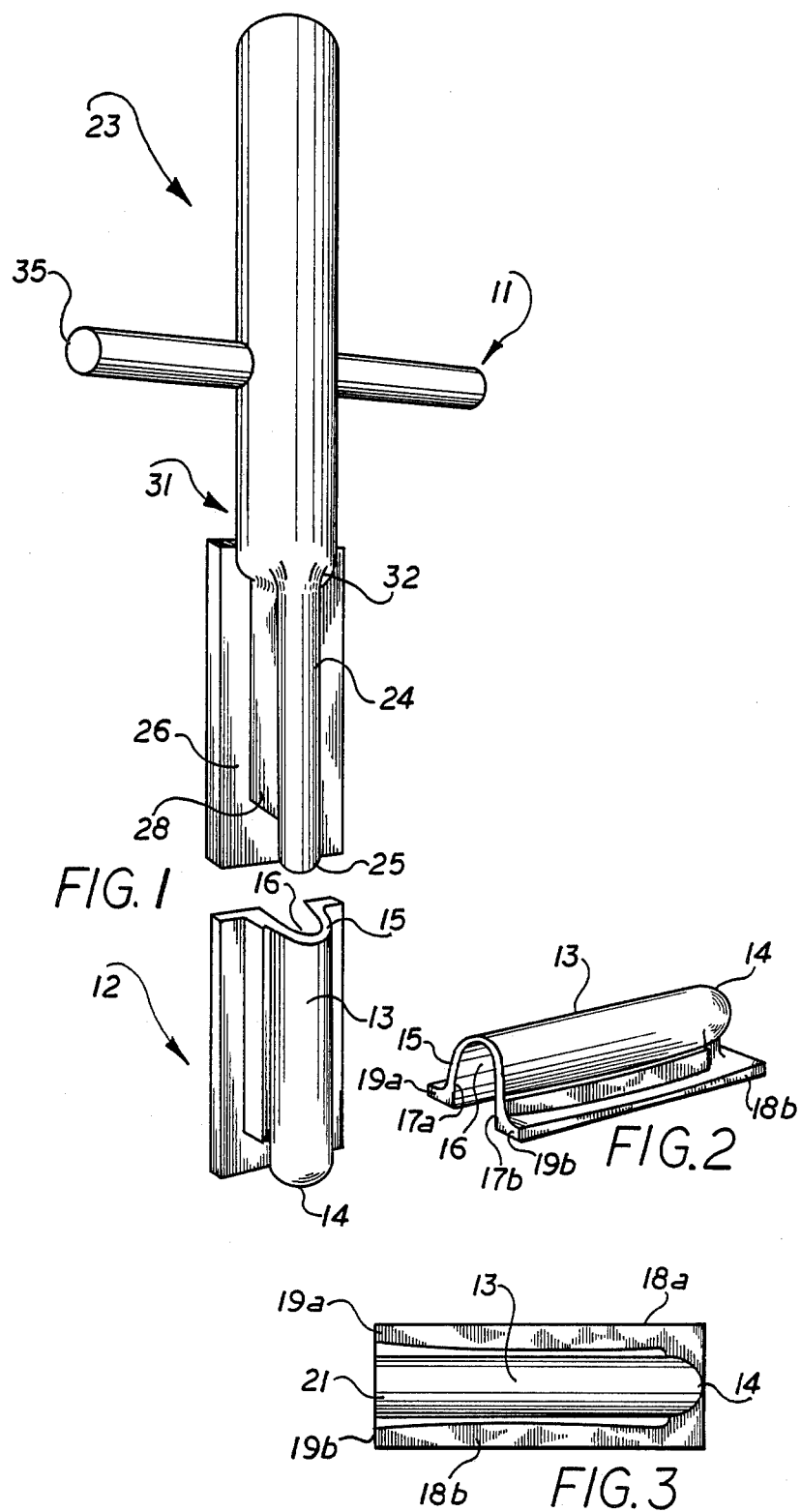

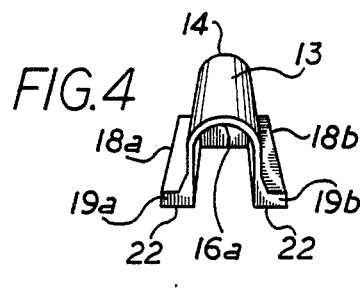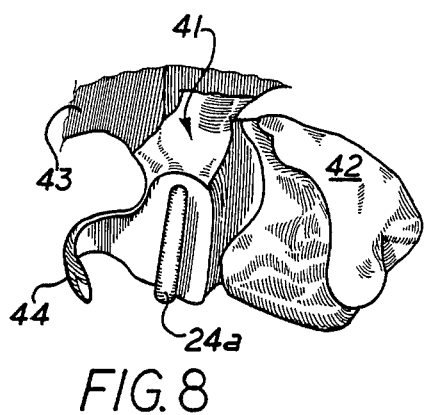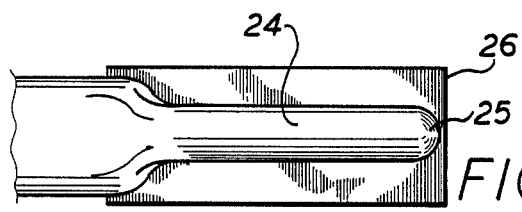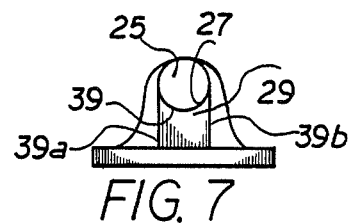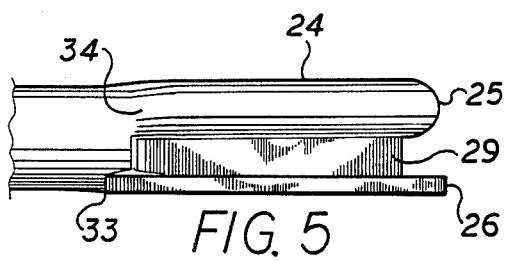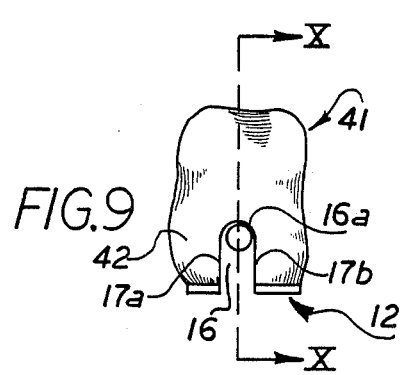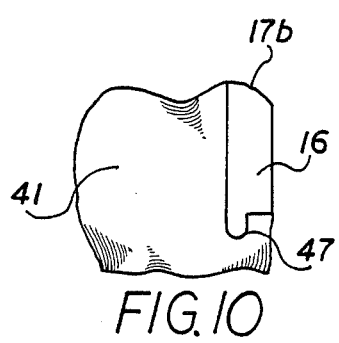

PRECISION ATTACHMENT FOR DENTURE CONSTRUCTION

FIELD OF THE INVENTION

This invention relates to the construction and mounting of partial dentures. In another aspect, it relates to a precision attachment which serves as a direct retainer of the partial or full denture made for support by abutment teeth.

BACKGROUND OF THE INVENTION

The individual component parts of partial dentures are the saddles, occlusal rests, direct and indirect retainers, and connectors. The saddle is that part of the partial denture which replaces lost alveolar tissue and carries the artificial teeth; they may be designated as free-end or bounded. In the former, an abutment is present only at the mesial (forward) end of the saddle; in the latter, an abutment tooth is present at both ends.

Precision attachments are one type of direct retainer, the principal other one being the clasp. Retainers function to provide positive retention to the denture; and second, to provide bracing for the denture against lateral forces and to transmit these forces to the abutment teeth. They may be more efficient than a clasp but the clinical circumstances in which they are required calls for a careful assessment. Where their use is indicated, the attachments currently used are commercially prefabricated and may be classified into several types. The present invention is directed to an improvement in the intracoronal precision type. Such attachments have two parts - male and female. The female part is in the form of slot that is embedded into some type of restoration, such as a crown or inlay in the abutment tooth. The male portion of the flange that fits into the slot and is attached into the saddle of the denture (see FIG. 9.42 of Osborn et al.). This type of attachment provides rigid connections between the tooth and the saddle and further serves the purposes of a retentive clasp arm, a bracing clasp arm and an occlusal rest, all in one unit. Disadvantages of the present attachments include: a) extensive preparation of the abutment tooth is necessary, and for free-end saddle dentures, a minimum of two teeth on each side of the arch must be prepared and splinted together. The chair side and laboratory preparation times required are substantial together. Together with the cost of the precious metal attachments themselves, this results in an expensive partial denture.

OBJECT OF THE INVENTION

It is a principal object of this invention to provide a novel semi-precision type of attachment, using male and female matching parts, which are completely absorbed during the high temperature casting process for the crown and partial denture. It is another object to provide attachment mating parts which are interchangeable rather than calling for the precision tolerances of the prior art metal parts. It is still a further object to provide an attachment which, because of its reduced dimensions, can be utilized on any abutment tooth, and in particular, on the canines, that have markedly small surfaces than the premolars.

Yet another object is the attachment that can be used as the free-end connector (normally a rigid bar or plate) in a broken-stress non-removable, partial denture. A still further object is a novel attachment which can stabilize the non-ridge connector in a broken-stress bridge (fixed partial denture). A yet further object is an attachment usable in either all tooth-borne (supported) or in a distal extension saddle (no natural teeth distal to the abutment tooth) removable partial dentures.

These and other objects are accomplished by the accompanying specification, beginning with a summary of the invention and a brief description of the drawing.

BRIEF SUMMARY OF THE INVENTION

Accordingly, there is provided a prosthesis construction assembly for use in placement and alignment of dental bridge components for the fabrication of human tooth replacements, comprising a rod-like female member adapted to be deposited in a cavity provided in the distal side of an anchor tooth comprising a longitudinal recess within said rod having two parallel side walls and a rounded mesial wall somewhat longer than the side walls so as to provide an end well in which a male member can pivot during the biting stresses to be imposed on the replacement teeth, and wherein the recess presents an arched roof with parallel walls when viewed in a transverse section; a distally outwardly oriented first flange integral with the ends of the open face of the recess and defining an external planar surface except for the recess portion; and a male member comprising (i) a rod portion also with a rounded first end and being sized to permit its sliding engagement and retention within the recess of said female portion; (ii) an outwardly oriented second flange portion integral with one arc of the rod portion surface and not extending beyond the point of said first rounded end, said second flange adapted to provide a sliding abutment to the external surface of said first flange; (iii) an elongated bar portion integrally attached to the other end of said male portion and abutting the proximal end of said second flange, which bar serves as an upwardly positioned mandrel during manipulation of the female member for spatial orientation thereof during fabrication; and (iv) a transverse bar disposed intermediate the ends of the mandrel portion and pinned thereto which serves to permit manipulation of the assembly to attain the desired placement of the female portion relative to the sagittal plane of the prosthesis.

BRIEF DESCRIPTION OF THE DRAWINGS

FIG. 1 is an exploded perspective view of the two components of a preferred embodiment of the attachment invention vertically aligned as for mounting on the abutment tooth with a mandrel portion in an upwardly graspable orientation;

FIG. 2 is a side elevational view of the female component of the attachment;

FIG. 3 is a top plan view of the female component;

FIG. 4 is an end elevational view of the female component showing the cross-sectional appearance of the elongated recess;

FIG. 5 is an elevational view of the male (flanged) component of the attachment;

FIG. 6 is a top plan view of the male component;

FIG. 7 is a distal end elevational view of the male rod and flange part revealing its cross-sectional appearance for union with the female part when lodged in an abutment tooth;

FIG. 8 is a perspective view of the male portion (mandrel cut away) mounted on the lateral face of a partial denture and ready for insertion (upon inversion)

in the prepared recess (not shown) which is defined by embediment of the female part in the abutment tooth;

FIG. 9 is a top plan view of a molar tooth inlaid on the distal face with the female part of the attachment;

FIG. 10 is a vertical section along line X—X of the inlaid tooth of FIG. 9 showing the pivot point.

Referring now to the drawing wherein like parts have been designated by a like reference numeral, and to FIG. 1 in particular, in which a preferred form of the partial denture attachment assembly is shown.

The denture construction attachment, generally 11, consists of two mating parts. The first of these is a smaller female member generally 12, adapted to be positioned and secured in a cavity (not shown) provided on the face of an abutment tooth. It includes an elongated generally cylindrical rod 13, optionally having a rounded first end 14 and a distal flat second end 15. A longitudinal recess 16 is disposed fully within said rod. This presents a rounded arch recess 16b (FIG. 4) having parallel opposing side walls, 17a and 17b, when viewed in a transverse section, taken along line IV—IV of FIG. 2.

Hollow rod 13 is provided with an outwardly oriented first bilateral flange 18a and 18b, which is integral with the wall ends (19a and 19b) of the open face 21 of the recess 16. This defines an external planar surface 22, except for the break caused by the recess portion 16.

The other component is a larger male member, generally 23, comprising a smaller smooth rod portion 24, also preferrably with a rounded first end 25, it being sized to permit its sliding engagement and retention within the long recess 16, both lengthwise and transversely, of female component 12. There is an outwardly oriented second flanged portion 26 integral with one arc 27 of the rod surface (FIG. 7) with the flange end 28 extending slightly beyond the point of the rod's rounded end 25. Second flange 26 is adapted to provided for a sliding abutment with the external surface 22 of the first flange 18. The integration of arc 27 of solid rod 24 and flange 26 is conveniently provided by a longitudinally aligned cradle 29 disposed between them and provided with a concave upper surface 30 (FIG. 7) that abuts rod arc 27.

The preferably cylindrical, elongated handle portion, generally 31, is pinned to the proximal end 32 of solid rod portion 24, the proximal end 33 of the flange 26, and the proximal end 34 of cradle 29 (FIGS. 5 and 6).

Bar 31 serves as an upwardly positioned mandrel during manual manipulation of the male portion for spatial orientation thereof, to attain parallelism of abutting teeth during fabrication of the denture. A transverse bar 35 is disposed intermediate the ends 36 and 37 of the mandrel rod 31. It is pinned thereto and serves to permit manipulation of the attachment to attain desired placement of the female portion relative to the sagittal plane.

The typical dimensions of the attachment components in actual denture fabrication would run as follows: As to the female component 12, the well portion of the recess 16 will be 1.5 mm in length, an open face 21 width of 1 mm and an overall component recess 16 length of 5.5 mm. The parallel opposing side walls, 17a and 17b, are about 2 mm in height with arch 16a. The outward planar surface 22 is 7 mm in height and 3 mm in width with a flange 18 thickness of 0.5 mm.

As to the male component 23, the rounded end 25 extends about 1 mm beyond the distal end of cradle 29 and has an overall solid rod length of 6 mm. Contiguous flange 26 is 7 mm in height, 4 mm in width, and 0.5 mm thick.

The handle portion 31 of the male component 23, serving as a mandrel, is 22 mm in length, with a transverse bar 35 being 18 mm wide. This bar is necessarily perpendicular to portion 31 and offset but parallel to in the plane 38 of the flange 26.

In FIG. 8 is a perspective view of one of the male members 24a on which is already cemented a partial denture, generally 41, that includes artificial tooth 42, cross-arch support 43 and clasp 44 for the arch or tooth (not shown). This removable appliance would be joined in the mouth with a prepared anchor tooth (mating portion in place) as is shown in FIGS. 9 and 10.

The male and female portions of the novel attachment allow for frictional engagement of the parallel walls, 17a and 17b, of recess 16 with the parallel walls 39a and 39b of cradle 29, along with the sliding engagement of the flanged faces 22 and 26 in a vertical direction. There is no lateral or rotational movement of the male or female portions of the attachments when engaged. However, the attachment is so designed that there is possible a distal rotational movement of the male rod end 25 from the female portion 14 to allow for the functional displacement of the one from the other, and also to allow for functional displacement movements of the saddles, as in the case of a unilateral or bilateral distal extension, removable partial denture.

Referring to FIG. 9, there is shown a top plan view of a molar tooth generally with the female part generally 12 being already mounted as an inlay in the distal aspect 42 of the anchor tooth 41. The parallel walls 17a and 17b and arch 16 are evident and ready to engage the mating rod 24. By averting to FIG. 10, which is a vertical section of the attachment inlaid tooth of FIG. 9, taken along line X—X, elongated recess 16 with its pivoting well 47 to receive rotatably tip 25 of rod 24, is seen.

Both attachment components are made of a precision moldable, thermoplastic resin material, which is also chemically inert, and can regulated to produce the typical dimensions described above to fairly close tolerances, so as to permit interchangeability of molded components. Each mating part should be capable of being volatilized in the high temperature casting process. Suitable inert resins are the polyolefins, for example, polyethylene or polypropylene.

METHOD OF USE OF THE ATTACHMENT INVENTION

The versatility and indications for its use and accuracy, simplicity, rapidity of setup and economy, allow for ready acceptability of the novel attachment. When the attachment is selected for use in a specific case, the study cast prepared from the patient's mouth is analyzed for vertical parallelism of the abutments (to permit partial denture insertion and removal). Attachment lengths (a minimum of four mm) are outlined in pencil on the cast, where, and in which direction the attachments will be placed. The anchor teeth are prepared in the mouth, and the areas outlined on the study cast are used to guide the placement (by drilling) of the recessed cavities for the inlaid attachment.

The ensuing working guide model is again placed on the surveyor and the anchor teeth recess areas are analyzed for parallel placement of the attachments. Placement of the attachments are determined by placing the mandrel rod of the male portion into the surveyor arm (not shown). With the female portion in place on the male portion in the surveyor, placement of the position of the female portion of the attachment is determined for each tooth abutment. In the design of a bilateral, distal extension, removable partial denture abutment, the placement of the female portion is critical. The female portions when placed in crossarch abutment retainers must be parallel in both the vertical and sagittal directions.

Mandrel portion 31 of the male member allows for parallel vertical placement of the female portion 12 in cross-arch abutments on the surveyor.

The cross-arch rod 35 of the male portion allows for parallel placement of the female portion relative to the sagittal plane of the denture for cross-arch abutment on the same surveyor.

This necessary parallelism in both the vertical and sagittal planes allows the male cross-arch portion of the attachment, as placed in the framework of a removable partial denture, to pivot (rotate) distally about the pin well from the female portion of the cross-arch abutment, with gingival displacement of distal extension saddles of a removable partial denture. The female portion is waxed to place on the wax-up, as part of the wax pattern for the abutment retainer. The abutment retainer, wax pattern, with the female portion 12 as an integral part of it, is invested and cast. After casting and finishing, the casting is seated on the abutment die in the model, and it is again checked for accuracy and fit of the male portion of the attachment into the female portion.

When accuracy of the attachments (parallelism, etc.) is established and confirmed on the surveyor, the continuation and fabrication of the other parts of the denture may continue. Depending upon the use of the attachment, the male portion thereof may be cast as part of the pontic (replacement for absent tooth) directly in a brokenstress bridge.

In the case of the use of an attachment for a bilateral distal extension type of removable partial denture, the parallelism is established for the female portions of the cross-arch abutment retainers. The lingual (tongue-side) portions of these bilateral cross-arch abutment retainers waxed patterns are surveyor-carved to receive non-retentive lingual bracing arms, on the framework of the removable partial denture. A notch or dimple is cut into the wax of the non-retentive lingual surface on the mesial (front facing) aspect. The cast lingual arms of the framework of the removable partial denture, will, in turn, have a small raised bleb (boss) on the internal surface of the clasp to engage the notch or dimple in the non-retentive surface of the lingual surface of each cross-arch abutment retainer.

In the case of the use of the attachment with a removable partial denture, the male portion of the attachment can be cast separately, as part of the partial denture framework along with the clasp arm.

I claim:

1. A prosthesis construction assembly for use in placement and alignment of dental bridge components for the fabrication of human tooth replacements, comprising:
    a. a rod-like female member adapted to be deposited in a cavity provided in the distal side of an anchor tooth comprising a longitudinal recess within said rod having two parallel side walls and a rounded mesial wall somewhat longer than the side walls so as to provide an end well in which a male member can pivot during the biting stresses to be imposed on the replacement teeth and wherein the recess presents an arched roof with parallel walls when viewed in a transverse section;
    b. a distally outwardly oriented first flange integral with the ends of the open face of the recess and defining an external planar surface except for the recess portion;
    c. a male member comprising (i) a rod portion also with a rounded first end and being sized to permit its sliding engagement and retention within the recess of said female portion; (ii) an outwardly oriented second flange portion integral with one arc of the rod portion surface and not extending beyond the point of said first rounded end, said second flange adapted to provide a sliding abutment to the external surface of said first flange; (iii) an elongated bar portion integrally attached to the other end of said male portion and abutting the proximal end of said second flange, which bar serves as an upwardly positioned mandrel during manipulation of the female member for spatial orientation thereof during fabrication; and (iv) a transverse bar disposed intermediate the ends of the mandrel portion and pinned thereto which serves to permit manipulation of the assembly to attain the desired placement of the female portion relative to the sagittal plane of the prosthesis.

2. The assembly of claim 1 wherein the male and female portions are both fabricated from molded resin materials that are adapted to be volatilized in the crown fabrication process.

3. The assembly of claim 2 wherein the resin is selected from one of a moldable polyolefin resin selected from the group consisting of polycarbonate and polymethacrylate.

4. The assembly of claim 1 wherein the mandrel portion of the male member has a generally cylindrical cross section.

5. The assembly of claim 1 wherein the one arc of the rod portion of the male member has a generally cylindrical cross section.

* * * * *